(12) United States Patent
Found

(10) Patent No.: US 8,859,627 B2
(45) Date of Patent: *Oct. 14, 2014

(54) ANTI-MICROBIAL COMPOSITION

(75) Inventor: John Found, Cottelsoe (AU)

(73) Assignee: Wild Child, West Perth (AU)

( * ) Notice: Subject to any disclaimer, the term of this patent is extended or adjusted under 35 U.S.C. 154(b) by 799 days.

This patent is subject to a terminal disclaimer.

(21) Appl. No.: 12/739,491

(22) PCT Filed: Oct. 23, 2008

(86) PCT No.: PCT/AU2008/001564
§ 371 (c)(1),
(2), (4) Date: Oct. 4, 2010

(87) PCT Pub. No.: WO2009/052566
PCT Pub. Date: Apr. 30, 2009

(65) Prior Publication Data
US 2011/0028563 A1   Feb. 3, 2011

(30) Foreign Application Priority Data

Oct. 23, 2007   (AU) ................ 2007905803

(51) Int. Cl.
*A61K 31/045* (2006.01)
*A61K 31/04* (2006.01)
*A01N 33/12* (2006.01)
*A61K 31/14* (2006.01)

(52) U.S. Cl.
CPC ............... *A01N 33/12* (2013.01); *A61K 31/14* (2013.01); *A61K 31/045* (2013.01)
USPC ......................................... 514/724; 514/740

(58) Field of Classification Search
None
See application file for complete search history.

(56) References Cited

U.S. PATENT DOCUMENTS

| | | | |
|---|---|---|---|
| 7,179,849 B2 * | 2/2007 | Terry | ............................ 523/122 |
| 2006/0269485 A1 | 11/2006 | Friedman et al. | |
| 2007/0207965 A1 | 9/2007 | Cuesta et al. | |
| 2007/0275064 A1 | 11/2007 | Mumoli | |

FOREIGN PATENT DOCUMENTS

| | | |
|---|---|---|
| WO | WO-2005/009352 A2 | 2/2005 |
| WO | WO 2005009352 A2 * | 2/2005 |
| WO | WO 2007056813 A1 * | 5/2007 |
| WO | WO-2007/066149 A2 | 6/2007 |
| WO | WO-2007/070795 A2 | 6/2007 |

OTHER PUBLICATIONS

Committee for Veterinary Medicinal Products Cetrimide Summary Report, The European Agency for the Evaluation of Medicinal Products, Mar. 1996, available at http://www.ema.europa.eu/docs/en_GB/document_library/Maximum_Residue_Limits_-_Report/2009/11/WC500012001.pdf.*
U.S. Appl. No. 12/093,985, filed May 2008, Found.*
El-Nima, E.I. "The Syngergism Between Centrimide and Antibiotics Against Pseudomonas Aeruginosa" Zbl. Bakt. Hyg. A. 258:120-127 (1984).

* cited by examiner

*Primary Examiner* — Svetlana M Ivanova

(74) *Attorney, Agent, or Firm* — Mintz Levin Cohn Ferris Glovsky and Popeo, P.C.; Ingrid A. Beattie

(57) ABSTRACT

The present invention relates to an anti-microbial composition and method of use thereof. In particular, the present invention relates to an anti microbial composition comprising farnesol and cetrimide.

29 Claims, 1 Drawing Sheet

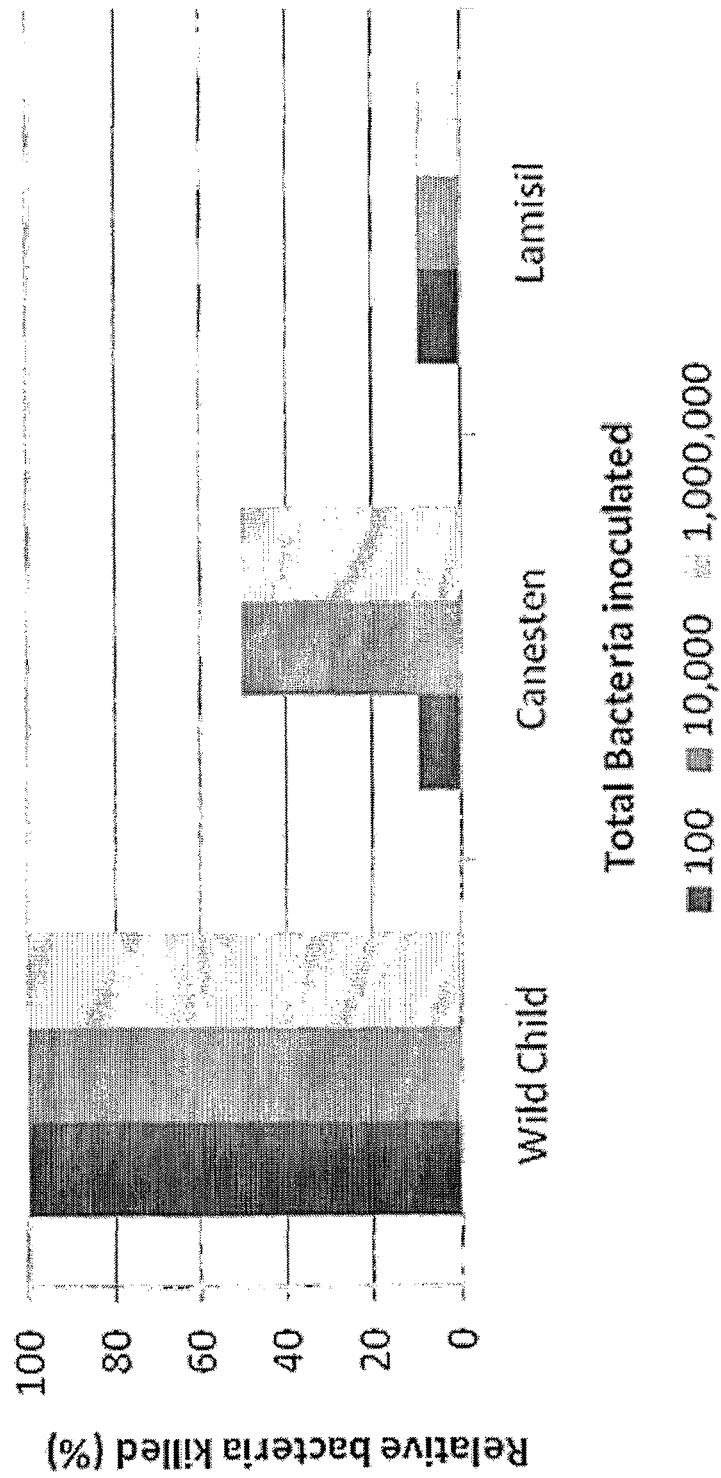

ANTI-MICROBIAL COMPOSITION

FIELD

The present invention relates to an anti-microbial composition and method of use thereof. In particular, the present invention relates to an anti-microbial composition comprising farnesol and cetrimide.

BACKGROUND

Since their discovery during the 20$^{th}$ century, antimicrobial agents (antibiotics and related medicinal drugs) have substantially reduced the threat posed by infectious diseases. However, it is well documented that in recent times numerous microbes, in particular bacteria, have become resistant to particular antimicrobial agents due to their overuse. Accordingly, there is a continuing need for new anti-microbial agents.

One area that is of particular important is in the area of infection control. Practices, such as hand washing and changing gloves before and after contact with subjects infected with microbes, are critically important in maintaining sterile environments and restricting the spread of disease. Antimicrobial agents, in particular antiseptics, are often used in these environments; however, their continued use has also seen a reduction in their efficacy.

Consequently there is a need for a general use antimicrobial agent that can be used in clinical settings i.e. the treatment of infections, wounds and the like as well as in general infection control e.g. cleaning/sterilising hard surfaces, hand washing and instrument treatment.

SUMMARY

The inventor has surprisingly found that an agent comprising an effective amount of farnesol and/or nerolidol and cetrimide has a synergistic antimicrobial action on a wide range of microbes including bacteria and fungi.

Accordingly, in a first aspect the present invention provides an antimicrobial agent comprising farnesol and/or nerolidol and cetrimide.

In a second aspect the present invention provides an antimicrobial agent consisting essentially of farnesol and/or nerolidol and cetrimide.

In some embodiments, the farnesol and/or nerolidol is derived or isolated from sandalwood oil, especially sandalwood oil extracted from Australian sandalwood (*Santalum spicatum*).

In some embodiments, the farnesol and nerolidol are present as an organically synthesised chemical substance.

The agents of the present invention may further comprise essential oils such as geranium oil, lavender oil and eucalyptus oil. These essential oils may assist the antimicrobial activity of the agents of the invention by, for example, helping the agents to penetrate the cell walls.

The agents may also be mixed with conventionally acceptable excipients, stabilizers, diluents or extenders usable in the art. If desired, adjuvants such as surfactants, stabilizers and antifoaming agents may also be added.

In some embodiments, the antimicrobial agent of the present invention further comprise from about 1% to about 10% of a stabilizer selected from the group consisting of glyceryl monostearate, stearic acid, triethanolamne, ethanol, polysorbate 20, cetyl alcohol, stearyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetum, glyceryl stearate, xanthan gum, geranium oil, lavender oil, eucalyptus oil, tea tree oil, lemon oil, anise oil, DEA cetyl phosphate, sodium stearate, potassium stearate, wool alcohols, octyl stearate, carnauba wax, ozokerite, carbomer, phenoxyethanol, methyl parabens and propyl parabens and mixtures thereof The formulation of the agents will depend upon the end use and methods of developing such formulations are well within the skill of persons in the art. Formulations include creams, shampoos, ointments, aqueous suspensions and dispersions, oily dispersions, pastes, dusting powders, wettable powders flowables, granules, aerosols and emulsions.

In some embodiments, the concentration of farnesol or nerolidol used is less than about 3%$^w/_w$.

In a third aspect, the present invention provides a method of forming the antimicrobial agent of the first and second aspects comprising the step of mixing at least farnesol and/or nerolidol with cetrimide.

In a fourth aspect, the present invention provides a method of disinfection comprising applying to a surface to be disinfected an antimicrobial agent according to the first and second aspects.

In a fifth aspect, the present invention provides a method of imparting antimicrobial protection to an object, comprising the step of applying to said object an effective protecting amount of an antimicrobial agent according to the first and second aspects In some embodiments, the object is a medical device selected from the group consisting of a medical implant, a wound care device, a personal protection device and a body cavity device.

In a sixth aspect, the present invention provides a method for treating or preventing a microbial infection in a mammal, comprising the step of applying to said mammal an antimicrobial agent according to the first and second aspects.

In some embodiment, the agent is applied to an infected part of said mammal. In some embodiments, the infected part will be skin or mucous membranes of said mammal.

In a seventh aspect, the present invention provides a method for producing an antimicrobial effect on skin, comprising applying to said skin an effective amount of the agent of the first or second aspects.

The antimicrobial agent may be applied either directly to intact skin or applied to mucous membranes which may be oral, nasal, vaginal or rectal cavities.

In an eighth aspect, the present invention provides a method for treating or preventing topical skin infection comprising contacting the skin with an antimicrobial agent according to the first and second aspects.

In a ninth aspect the present invention provides use of a agent comprising farnesol and/or nerolidol and cetrimide for the treatment or prevention of a microbial infection.

In a tenth aspect the present invention provides the use of an agent comprising farnesol and/or nerolidol and cetrimide in the manufacture of a medicament for the treatment of a microbial infection.

In an eleventh aspect the present invention provides a method for sterilizing a surface comprising the step of applying to said surface an antimicrobial agent of the first or second aspects.

The antimicrobial agent of the present invention is effective against a large range of microorganisms; however, it is especially suited for the treatment of fungal conditions caused by *Candida* sp, in particular *Candida albicans*.

It will be appreciated by those skilled in the art that the antimicrobial agent can be applied to any animal or object which is likely to come into contact with microbes.

BRIEF DESCRIPTION OF THE FIGURES

FIG. 1 shows comparative kill rates for the farnesol/cetrimide composition of the present invention against *Candida albicans*.

DETAILED DESCRIPTION OF THE PREFERRED EMBODIMENTS

All publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention employs, unless otherwise indicated, conventional chemistry within the skill of the art. Such techniques are well known to the skilled worker, and are explained fully in the literature. See, eg., Vogel and Furniss, 1989, "Vogel's textbook of practical organic chemistry", Longman Publishers; 1979; and Huheey, J., 1983, "Inorganic Chemistry $3^{rd}$ Edition", Harper International.

The description that follows makes use of a number of terms used in chemistry. Unless defined otherwise, all technical and scientific terms used herein have the meaning commonly understood by a person skilled in the art to which this invention belongs. The following references provide one of skill with a general definition of many of the terms used in this invention: "The Cambridge Dictionary of Science and Technology" (Walker ed., 1988); Hale & Marham, "The Harper Collins Dictionary of Biology" (1991); "Nomenclature of organic chemistry" $4^{th}$ Edition Pergamon Publishers (1979); "Henderson's dictionary of biological terms" (Lawrence, Eleanor (ed.)) $12^{th}$ Edition, Prentice Hall Publishers (2000); and "Oxford Dictionary of Chemistry", $4^{th}$ Edition, (Daintith, John (ed)) 2000, Oxford University Press.

Generally, the nomenclature and the laboratory procedures used in chemistry as described herein are those well known and commonly employed in the art.

It is understood that the invention is not limited to the particular materials and methods described, as these may vary. It is also to be understood that the terminology used herein is for the purpose of describing particular embodiments only, and it is not intended to limit the scope of the present invention which will be limited only by the appended claims. It must be noted that as used herein and in the appended claims, the singular forms "a", "an", and "the" include plural reference unless the context clearly dictates otherwise. Thus, for example, a reference to "a compound" includes a plurality of such compounds and "an agent" includes a plurality of such agents. Although any materials and methods similar or equivalent to those described herein can be used to practice or test the present invention, the preferred materials and methods are now described.

In its broadest aspect the present invention is directed towards an antimicrobial agent comprising farnesol and/or nerolidol and cetrimide.

As used herein, the terms "antimicrobial agent" or "antimicrobial agents," "antimicrobial," "antibacterial," "antifungal" and grammatical equivalent terms refer to a composition or agent of the present invention which is capable of inhibiting the growth of a microorganism or kill a microorganism. Antimicrobial agents can have microbial-static effects and/or microbial-cidal effects.

The "antimicrobial agents" of the present invention comprise or consist essentially of farnesol and/or nerolidol and cetrimide, which agents are capable of decreasing the number of live microbes on the surface of an object or the skin of a subject.

The term "microbes" or "microbial" as used herein refers to species of bacteria, fungi, viruses and protozoa that can treatable with the antimicrobial agents of the present invention. For example, the "antimicrobial agents" of the present invention are useful against bacterial cells such as gram positive bacteria including, but not limited to, a *Bacillus* species, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* species, e.g., *Streptomyces lividans*, *Streptomyces murinus*, and *Streptococcus pneumoniae*; or *Staphylococcus* species such as *Staphylococcus aureus* and *Staphylococcus epidermidis*; *Enterococcus* species such as *Enterococcus faecium*; or gram negative bacteria such as *Salmonella* species such as *Salmonella typhi*; *Escherichia* species such as *Escherichia coli*; *Vibrio* species such as *Vibrio cholerae*; *Neisseria* species, such as *Neisseria meningitidis* and *Neisseria* gonorrhoea; and *Pseudomonas* sp such as *Pseudomonas aeruginosa*.

The "antimicrobial agents" of the present invention are also useful against fungal cells. The term "fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In some embodiments, the fungal cell is a yeast cell. "Yeast" as used herein includes ascosporogenous yeast (Endomycetales), basidiosporogenous yeast, and yeast belonging to the fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980). In some embodiments, the yeast cell is a *Candida*, *Hansenula*, *Kluyveromyces*, *Pichia*, *Saccharomyces*, *Schizosaccharomyces*, *Yarrowia*, *Trichophyton* or *Epidermophyton* cell. In some embodiments, the yeast cell is *Candida albicans*.

In other embodiments, the fungal cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic.

The "antimicrobial agents" of the present invention are also useful against viruses such as Human Immunodeficiency Virus (HIV), Human Papilloma Virus (HPV) and Herpes Simplex Virus (HSV).

The "antimicrobial agents" of the present invention are also useful against protozoan species including *Chlamydia trachomatis* and *Trichomonas vaginalis*.

The concentration of farnesol, nerolidol and cetrimide in the antimicrobial agent is described as an "effective amount". The term "effective amount" means an amount of the agent comprising farnesol, nerolidol and cetrimide sufficient to decrease the number of microbes. The effective amount can typically range from about 2 ppm to about 3% (15000-30000 ppm). This amount can vary depending on with farnesol and/or nerolidol is used together with the cetrimide, the form of agent used (e.g., cream, lotion and the like), the microbial species targeted, and other parameters that would be apparent to one of skill in the art. One of skill in the art would readily be able to determine the effective amount for a given application based on the general knowledge in the art and guidance provided in the procedures in the Examples given below. In one example, farnesol is used in an amount of approximately 5,000 ppm.

Concentrations of farnesol or nerolidol of about, for example, 2, 20, 30, 40, 50, 60, 70, 80, 90, 100, 110, 125, 130, 140, 150, 175, 200, 225, 250, 300, 350, 400, 450, 500, 600, 750, 800, 1000, 1100, 1250, 1425, 1500, 1750, 2000, 2250, 2500, 3000, 3500, 4000, 4250, 4500, or 4750 ppm can be used as effective amounts in the agents and methods of the current invention.

Concentrations of any other ingredients or components can also be readily determined by one of skill in the art using methods known in the art and demonstrated below. However, when the term "effective amount" is used in reference to solvents, solubilizing agents or solutions, the term means that the solvents solubilize the antimicrobial agent and also that the solution has a concentration that effectively controls the microbes being treated.

In some embodiments, the present invention provides an antimicrobial agent consisting essentially of farnesol and/or nerolidol and cetrimide or their derivatives and a suitable carrier. In some embodiments, the antimicrobial agent consists of or consists essentially of farnesol and cetrimide and a suitable carrier.

The agents of the present invention can further comprise additional ingredients. For example, water or any animal-compatible diluent or carrier, surfactants (cleansing, emulsifying and/or foam-boosting surfactants), humectants, buffering agents, chelating agents, preservatives, pH Adjusters, moisturizers, antioxidants, conditioning agents, adjuvants, stabilizers and vehicles.

In other embodiments, "emulsifying surfactants" are incorporated into the antimicrobial agent. Emulsifying surfactants include compounds that reduce the surface tension and the emulsifying surfactants are used in an amount which produces the desired function provided that the amount does not affect the stability of the farnesol/nerolidol/cetrimide antimicrobial agent. They create barriers around droplets to prevent them from coalescing. Emulsifiers could be, but are not limited to oil-in-water emulsifiers, water-in-oil emulsifiers, water-in-oil-in-water emulsifiers, oil-in-water-in-oil emulsifiers, silicone-in-water emulsifiers, and water-in-silicone emulsifiers. Examples include, but are not limited to, glyceryl trioleate, acetylated sucrose distearate, sorbitan trioleate, polyoxyethylene (1) monostearate, glycerol monooleate, sucrose distearate, polyethylene glycol (50) monostearate, octyl phenoxypoly (ethyleneoxy) ethanol, deacylerin pentaisostearate, sorbitan sesquioleate, hydroxylated lanolin, lanolin, triglyceryl diisostearate, polyoxyethylene (2) oleyl ether, calcium stearoyl-2-lactylate, cetearyl glucoside, methyl glucoside sesquistearate, sorbitan monopalmitate, methoxy polyethylene glycol-22/dodecyl glycol copolymer, polyethylene glycol-45/dodecyl glycol copolymer, polyethylene glycol 400 distearate and glyceryl stearate, cetyl phosphate, potassium cetyl phosphate. See also CFTA Dictionary 1796-1803.

In some embodiments, the antimicrobial agents of the present invention are used to treat the skin of an animal, as such it may be desirable to include "conditioning agents" in the formulations. Skin conditioning agents can be used. Skin conditioning agents include compounds that soften and smooth the skin and in an amount which produces the desired function provided that the amount does not affect the stability of the farnesol/nerolidol/cetrimide antimicrobial composition. These compounds achieve this effect by lubricating the skin surface, encouraging skin water retention, and altering product textures. Examples include, but are not limited to, octyl hydroxystearate, lanolin, capric/caprylic triglyceride, cetyl palmitate, cetyl alcohol, isopropyl isostearate, glyceryl dilaurate, isopropyl myristate, palm alcohol, and sucrose cocoate. See also CTFA Dictionary 1768-1773.

In some embodiments, humectants are also incorporated into the antimicrobial agents of the present invention. What is meant by "humectants" is one or more compounds that prevent the skin from losing moisture and the humectants are used in an amount which produces the desired function provided that the amount does not affect the stability of the sesquiterpene alcohols. Examples include, but are not limited to, glycerin, glucose, honey, lactic acid, polyethylene glycol, propylene glycol, sorbitol, sucrose, and trehalose. See also CFTA Dictionary 1773-1774.

If buffering agents are required then compounds that can maintain a desired pH in an aqueous environment are used. Examples include, but are not limited to, boric acid, citric acid, lactic acid, fumaric acid, phosphoric acid, and salts thereof. See also CFTA Dictionary 1733-1734.

In some embodiments, it may be desirable to use "chelating agents", which are compounds that can complex and subsequently inactivate ions in the antimicrobial agents and the chelating agents are used in an amount which produces the desired function provided that the amount does not affect the stability of the farnesol/nerolidol/cetrimide antimicrobial agent. Examples include citric acid, disodium edetate, pentapotassium triphosphate, and phytic acid. See also CFTA Dictionary 1734-1735.

Once the required antimicrobial agents are prepared then in some embodiments "preservatives" are included to prevent or reduce or slow down microbial growth of those species that are not sensitive to the invention. The amount of preservative used will depend upon the preservative used and is well within the skill of the art to determine. Examples include, but are not limited to, benzoic acid, butylparaben, ethylparaben, propylparaben, methylparaben, sorbic acid, phenoxyethanol, and triclosan. See CFTA Dictionary 1765-1766.

pH Adjusters are also present in some embodiments of the invention and the pH Adjusters are used in an amount which produces the desired function provided that the amount does not effect the stability of the farnesol/nerolidol/cetrimide antimicrobial agents. "pH adjuster" are acids or bases that can be used to adjust the pH of the finished antimicrobial agent to the desired level. Examples include, but are not limited to, acetic acid, ammonia, citric acid, ethanolamine, formic acid, oxalic acid, potassium hydroxide, sodium hydroxide, and triethanolamine. See CFTA Dictionary 1764.

Further embodiments of the antimicrobial agents of the present invention may include one or more moisturizers, preferably propylene glycol and the moisturizers are used in an amount which produces the desired function provided that the amount does not affect the stability of the sesquiterpene alcohols. Additionally, emulsifying agents may be desirable, preferably Ceteareth-20, manufactured by Promateen Chemicals Inc., which is a polyethylene glycol ether of cetearyl alcohol. Ceteareth-20 has 20 moles of ethylene oxide which is added to the non-ionic surfactant to increase its water solubility. In the event that an emulsion stabilizer is used, the preferred one is a mixture of cetyl and stearyl alcohols, sold by Croda Inc. under the name Cetearyl alcohol.

In order to prevent the degradation caused by oxidation, antioxidants may be included in the antimicrobial agents and the antioxidants are used in an amount which produces the desired function provided that the amount does not affect the stability of the farnesol/nerolidol/cetrimide antimicrobial agents. Antioxidants include, but are not limited to free radical scavengers and reducing agents such as, acetyl cysteine, ascorbic acid, butylated hydroxytoluene, green tea extract, caffeic acid, cysteine, tocopherol, ubiquinone, and propyl gallate, preferably butylated hydroxytoluene ("BHT"). See CFTA Dictionary 1727.

In other embodiments, in addition to the farnesol/nerolidol/cetrimide, pH Adjusters, chelating agents, humectants and the like, the antimicrobial agents can further comprise adjuvants and the adjuvants are used in an amount which produces the desired function provided that the amount does not effect the stability of the farnesol/nerolidol/cetrimide antimicrobial agents. Examples of adjuvants include, but are not limited to vehicles, stabilizers, moisturizers, cleansing surfactants, emulsifying surfactants, emulsifying stabilizers, foam-boosting surfactants, emollient skin conditioning agents, humectants, hair conditioning agents, buffering agents, pH adjusters, chelating agents, antioxidants, preservatives, botanical extracts, fragrances, and dyes.

Stabilizers may also include, but are not limited to, $C_{10\text{-}30}$ Alkyl PEG-20 Itaconate copolymer, long chain acyl derivatives (including, but not, limited, to ethylene glycol distearate and ethylene glycol monostearate), esters of long chain fatty acids (including but not limited to stearyl stearate), alkyl dimethylamine oxides, methylcellulose, hydroxybutyl methylcellulose, hydroxypropylcellulose, hydroxypropyl methylcellulose, hydroxyethyl cellulose, distearyl phthalic amide (e.g. Stephan SAB-2), di(hydrogenated) tallow phthalic amide (e.g. Stephan TAB-2), primary amines with a fatty alkyl moiety of at least 16 carbons (including but not limited to palmitate amine or stearamine), polyacrylic acids, polysaccharide gums (including but not limited to Xanthan Gum), colloidal clays (including but not limited to benzyl dimethyl hydrogenated tallow ammonium montmorillonite), colloidal silica, triethanolamne, ethanol, cetyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetum, glyceryl stearate, xanthan gum, geranium oil, lavender oil, eucalyptus oil, tea tree oil, lemon oil, anise oil, DEA cetyl phosphate, wool alcohols, octyl stearate, carnauba wax, ozokerite, carbomer, phenoxyethanol, methyl parabens and propyl parabens and mixtures thereof. While the amount of stabilizer used can be readily determined by those skilled in the art, suitable ranges include between about 1% to about 10% v/v.

The antimicrobial agents of the present invention can be administered topically to an animal, by the direct laying on or spreading of the agents on the skin or mucous membranes, preferably of a mammal, most preferably of a human. The agents useful in the subject invention involve formulations suitable for topical application to mammalian skin or mucous membranes. Additionally, the agents may be made into a wide variety of product types. These include, but are not limited to solutions, aerosols, lotions, creams, gels, sticks, ointments, pastes, cream rinses, shampoos, and body washes. The preferred embodiments are creams Vehicles include, but are not limited to, water, propylene glycol, butylene glycol, ethanol, isopropanol, silicones. Preferably, the vehicle is water.

In some embodiments, the antimicrobial agents of the present invention may further include other known antimicrobials. Such agents are well known in the art and are present in many commercial antimicrobial compositions, including (without limitation) dichlorobenzyl alcohol, iodophors, thiomersal, clindamycin, erythromycin, benzoyl peroxide, bacitracin, polymyxin B, mupirocin, neomycin, triclosan, parachlorometaxylene, foscarnet, fluconazole, itriconazole, ketoconazole miconazole, iodine, sorbic acid, benzoic acid, dehydroacetic acid, propionic acid, methyl paraben, ethyl paraben, propyl paraben, butyl paraben, cetrimide, chlorhexidine (free base and/or salts), other biguanides, such as polyhexamethyl biguanide and chlorhexidine gluconate, chlorocresol, chloroxylenol, benzyl alcohol, bronopol, chlorbutol, ethanol, phenoxyethanol, phenylethyl alcohol, The methods of the present invention provide for topically contacting an agent as described above with the skin or mucous membranes or surfaces that have been in contact with pathogenic microbes.

The treatment methods of the invention are achieved by topically applying an agent as described above. The agent may be topically applied to the surface by, for example, pouring the agent on the surface, or rubbing the agent over the surface. When the agent is topically applied as described above, the agent should thoroughly saturate the surface. In order to thoroughly saturate the surface with the agent, a sufficient or adequate amount of agent should be employed.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The following examples, which describe exemplary techniques and experimental results, are provided for the purpose of illustrating the invention, and should not be construed as limiting.

Example 1

Anti-Microbial Composition

Four forms of anti-microbial composition were prepared:
Sample 1
A cream formulation comprising:

| | |
|---|---|
| Cetostearyl Alcohol | 7.5% |
| Citric Acid | 1.0% |
| Dimethicone 350 | 5.0% |
| Farnesol | 3.0% |
| Purified water | 83.5% |

Sample 2
A cream formulation comprising:

| | |
|---|---|
| Cetostearyl Alcohol | 7.5% |
| Cetrimide | 1.2% |

-continued

| | |
|---|---|
| Citric Acid | 1.0% |
| Dimethicone 350 | 5.0% |
| Purified water | 85.3% |

Sample 3
A cream formulation comprising:

| | |
|---|---|
| Cetostearyl Alcohol | 7.5% |
| Cetrimide | 1.2% |
| Citric Acid | 1.0% |
| Dimethicone 350 | 5.0% |
| Farnesol | 3.0% |
| Purified water | 82.3% |

Sample (4)

A sample of commercially available anti-fungal cream (Canesten™–1% clotrimazole).

A series of plates were then prepared containing an aliquot of sample (3) prepared in accordance with the preferred formula given above. The aliquot was suspended in tryptone soy agar. 1 g of the cream was emulsified into 5 mL of saline. A 2 mL aliquot was removed and serially diluted using saline. 6 mL of tryptone soy broth was then added to the suspensions. They were then added to 10 mL of molten double strength tryptone soy agar and plate poured. Once cooled the plates were inoculated with 94 cfu of S. aureus ATCC 6538P. The plates were then incubated at 32° C. for 5 days. Following the incubation the number of colonies of S. aureus isolated was then determined.

| Amount of Cream in plate | Number of colonies of S. aureus recovered |
|---|---|
| 1 g | Nil |
| 0.4 g | Nil |
| 0.2 g | Nil |
| 0.1 g | Nil |
| 0.05 g | Nil |
| 0.025 g | Nil |
| 0.0125 g | Nil |
| 0.00625 g | Nil |

It was observed that farnesol showed synergistic antimicrobial effects when combined with cetrimide.

Example 2

Evaluation of the Antimicrobial Action-Study 2

A trial was conducted on a cream base containing (1) farnesol but no cetrimide; (2) cetrimide but no farnesol; (3) farnesol and cetrimide. As a control measure a commercially available anti-fungal cream (Canesten™ 1% clotrimazole) (4) was trialled using the same method.

Approximately 1 g of each cream sample was emulsified with 1 g of liquid paraffin. 10 ml of water was added to this and vigorously shaken. The cream was then added to 10 ml of molten (44° C.) double strength tryptone soy agar (TSA) and a poured into standard microbiology plate. While the plate was cooling the fungi were harvested and a heavy inoculum prepared. A series of dilutions were prepared of the primary inoculum. Three suspensions were used: inoculums 2 & 3 were 1:100 dilutions of the previous suspension. 100 µL of these suspensions were lawn inoculated onto each plate. Of particular note was the actual integrity of the plate. Following incubation the plates were examined. Where growth was present, enumeration of the isolates was often not possible due to heavy growth; however a semi-quantitative method was employed.

Candida albicans ATCC 10231

| No of organisms | (1) | (2) | (3) | (4) |
|---|---|---|---|---|
| $10^7$ | *** | ** | occ | ** |
| $10^5$ | *** | occ | NG | ** |
| $10^3$ | *** | NG | NG | NG |

Trichophyton mentagrophytes

| No of organisms | (1) | (2) | (3) | (4) |
|---|---|---|---|---|
| $10^6$ | NG | NG | NG | NG |
| $10^4$ | NG | NG | NG | NG |
| $10^2$ | NG | NG | NG | NG |

Epidermophyton floccossum

| No of organisms | (1) | (2) | (3) | (4) |
|---|---|---|---|---|
| $10^4$ | NG | NG | NG | NG |
| $10^2$ | NG | NG | NG | NG |
| $10^0$ | NG | NG | NG | NG |

*** = heavy growth
** = moderate growth
occ = occasional isolates
NG = No growth It can be seen that, in the case of Candida albicans (1) farnesol had very little effect on the numbers of viable bacteria (2) cetrimide alone had a moderate effect on the numbers of viable organisms. The combination of farnesol and cetrimide (3) was more anti-microbial than either of the former and the control product.

Example 3

Evaluation Against Two Commercial Products

Sample 3 as described in Example containing as active agents ~30 mg of farnosol/g and ~30 mg of cetrimide/g was made up for microbial analysis. Samples were obtained of commercially available Canesten™, containing 10 mg/g chlotrimazole, and Lamisil™, containing 10 mg/g of terbinafine hydrochloride. One gram of each product was added to individual aliquots of 10 mL of double strength liquid Tryptic Soy Agar (TSA) at 44° C. The mixture was then transferred to a microbiological petri dish known as a "plate". While the plate was cooling a standard culture of Candida sp. fungi was harvested and a heavy inoculum prepared. A series of dilutions was prepared from the primary inoculum, 100 mL of these suspensions were lawn inoculated onto each plate. All plates were incubated at 32° C. for 5 days and then 23° C. for a further 5 days. Following incubation the plates were examined and a semi-quantitative assessment was made.

| Organism | Total number of bacteria inoculated (cfu) | Sample 3 30 mg/g | Canesten ™ 10 mg/g chlotrimazole | Lamisil ™ 10 mg/g terbinafine HCl |
|---|---|---|---|---|
| Candida albicans ATCC 10231 | $10^6$ | No growth | Moderate growth | Heavy growth |
| | $10^4$ | No growth | Moderate growth | Heavy growth |
| | $10^2$ | No growth | Heavy growth | Heavy growth |
| Trichophyton mentagrophytes | $10^5$ | No growth | No growth | No growth |
| | $10^3$ | No growth | No growth | No growth |
| | 86 | No growth | No growth | No growth |
| Microsporum canis | $10^2$ | No growth | No growth | No growth |
| | 26 | No growth | No growth | No growth |

It can be seen that sample 3 shows efficacy equivalent to chlotrimazole and terbinafine when trialled against the *trichophyton* and *microsporum* species know to be responsible for tinea. Also sample 3 appears to be much more effective against the causative organism for thrush (*Candida albicans*) by several orders of magnitude.

The claims defining the invention are as follows:

1. An antimicrobial agent consisting of farnesol and cetrimide and one or more of:
   (a) a stabilizer, wherein the stabilizer is selected from the group consisting of glyceryl monostearate, stearic acid, triethanolamne, ethanol, polysorbate 20, cetyl alcohol, stearyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetum, glyceryl stearate, xanthan gum, geranium oil, lavender oil, eucalyptus oil, tea tree oil, lemon oil, anise oil, DEA cetyl phosphate, sodium stearate, potassium stearate, wool alcohols, octyl stearate, carnauba wax, ozokerite, carbomer, phenoxyethanol, methyl parabens, propyl parabens and mixtures thereof;
   (b) an excipient, wherein the excipient is selected from the group consisting of lavender oil, eucalyptus oil, olive oil, lemon oil, verbena oil, geranium oil, anise oil, patchouli oil, lavender oil, boronia oil, eucalyptus oil, tea tree oil, bay oil, sandalwood oil, orange oil, citronella oil, grapefruit oil, jasmine oil, cinnamon oil, chamomile oil, clary sage oil, lime oil, mandarin oil, palma rosa oil, rosewood oil, ylang ylang oil, hazelnut oil, nutmeg oil and mixtures thereof; and
   (c) a carrier, wherein the carrier is water.

2. The agent of claim 1, wherein the farnesol is isolated from Australian sandalwood oil.

3. The agent of claim 1, which consists of:
   (a) from about 0.1% to about 5.0% of farnesol;
   (b) from about 0.1% to about 5.0% of cetrimide;
   (c) from about 1% to about 10% of said stabilizer;
   (d) from about 0.5% to about 5% of said excipient; and
   (e) from about 80% to about 95% of said carrier.

4. A method of forming the antimicrobial agent of claim 1 comprising the step of mixing said farnesol and cetrimide with one or more of:
   a) the stabilizer,
   b) the excipient, and
   c) the carrier.

5. A method of disinfection comprising applying to the surface of an object to be disinfected an effective amount of the antimicrobial agent of claim 1.

6. The method of claim 5, wherein the object is a medical device selected from the group consisting of a medical implant, a wound care device, a personal protection device and a body cavity device.

7. An antimicrobial agent consisting of:
   (a) from about 0.1% to about 5.0% of farnesol isolated from Australian sandalwood oil;
   (b) from about 0.1% to about 5.0% of cetrimide;
   (c) from about 1% to about 10% of a stabilizer selected from the group consisting of dimethicone, cetostearyl alcohol, citric acid and mixtures thereof;
   (d) from about 0.5% to about 5% of an excipient; and
   (e) from about 80% to about 95% water.

8. The antimicrobial agent of claim 1, wherein the concentration of farnesol is less than about 3% weight by weight.

9. The antimicrobial agent of claim 1, wherein the farnesol is present as an organically synthesized chemical substance.

10. The antimicrobial agent of claim 1, wherein the antimicrobial agent is formulated into a cream, shampoo, ointment, aqueous suspension, aqueous dispersion, oily dispersion, paste, dusting powder, wettable powder, granule, aerosol, or emulsion.

11. The method of claim 5, wherein the antimicrobial agent decreases the number of live microbes on the surface of the object.

12. The method of claim 5, wherein the antimicrobial agent has antimicrobial activity against a bacterium, fungus, virus, or protozoan.

13. The method of claim 12, wherein the bacterium comprises a gram positive bacterium.

14. The method of claim 13, wherein the bacterium comprises a *Bacillus* species, a *Streptomyces* species, a *Staphylococcus* species, or an *Enterococcus* species.

15. The method of claim 14, wherein the bacterium comprises *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis, Bacillus thuringiensis, Streptomyces lividans, Streptomyces murinus, Streptococcus pneumonia, Staphylococcus aureus, Staphylococcus epidermidis,* or *Enterococcus faecium.*

16. The method of claim 12, wherein the bacterium comprises a gram negative bacterium.

17. The method of claim 16, wherein the bacterium comprises a *Salmonella* species, an *Escherichia* species, a *Vibrio* species, a *Neisseria* species, or a *Pseudomonas* species.

18. The method of claim 17, wherein the bacterium comprises *Salmonella typhi, Escherichia coli, Vibrio cholera, Neisseria meningitides, Neisseria gonorrhoea,* or *Pseudomonas aeruginosa.*

19. The method of claim 12, wherein the fungus comprises a *Ascomycota, Basidiomycota, Chytridiomycota,* or *Zygomycota* cell.

20. The method of claim 12, wherein the fungus comprises a yeast.

21. The method of claim 20, wherein the yeast comprises an ascosporogenous yeast, a basidiosporogenous yeast, or a blastomycetes yeast.

22. The method of claim 20, wherein the yeast comprises a *Candida,* a *Hansenula,* a *Kluyveromyces,* a *Pichia,* a *Saccharomyces,* a *Schizosaccharomyces,* a *Yarrowia,* a *Trichophyton,* or a *Epidermophyton* cell.

23. The method of claim 22, wherein the yeast comprises a *Candida albicans* cell.

24. The method of claim 12, wherein the fungus comprises a filamentous fungus.

25. The method of claim 24, wherein the fungus comprises a Eumycota or Oomycota cell.

26. The method of claim 12, wherein the virus comprises a Human Immunodeficiency Virus (HIV), a Human Papilloma Virus (HPV), or a Herpes Simplex Virus (HSV).

27. The method of claim 12, wherein the protozoan comprises *Chlamydia trachomatis* or *Trichomonas vaginalis*.

28. A method of imparting antimicrobial protection to an object, comprising applying to the object an effective protecting amount of the antimicrobial agent of claim 1.

29. The method of claim 28, wherein the antimicrobial agent comprises antimicrobial protection against a bacterium, fungus, virus, or protozoan.

\* \* \* \* \*